US011497628B2

United States Patent
Etenzi et al.

(10) Patent No.: US 11,497,628 B2
(45) Date of Patent: Nov. 15, 2022

(54) WEARABLE ASSISTED-WALKING DEVICE

(71) Applicants: SCUOLA SUPERIORE SANT'ANNA, Pisa (IT); THE REGENTS OF THE UNIVERSITY OF COLORADO, Denver, CO (US)

(72) Inventors: Ettore Etenzi, Terricciola (IT); Alena Marie Grabowski, Boulder, CO (US); Vito Monaco, Pisa (IT); Silvestro Micera, Florence (IT)

(73) Assignees: SCUOLA SUPERIORE SANTANNA, Pisa (IT); THE REGENTS OF THE UNIVIERSITY OF COLORADO, A BODY CORPORATE, Denver, CO (US)

( * ) Notice: Subject to any disclaimer, the term of this patent is extended or adjusted under 35 U.S.C. 154(b) by 265 days.

(21) Appl. No.: 16/633,647

(22) PCT Filed: Jul. 19, 2018

(86) PCT No.: PCT/IB2018/055382
§ 371 (c)(1),
(2) Date: Jan. 24, 2020

(87) PCT Pub. No.: WO2019/021126
PCT Pub. Date: Jan. 31, 2019

(65) Prior Publication Data
US 2020/0170809 A1    Jun. 4, 2020

(30) Foreign Application Priority Data

Jul. 24, 2017 (IT) .................. 102017000084346

(51) Int. Cl.
*A61F 2/68* (2006.01)
*A61H 1/02* (2006.01)
(Continued)

(52) U.S. Cl.
CPC .................. *A61F 2/68* (2013.01); *A61F 2/66* (2013.01); *A61H 1/0266* (2013.01);
(Continued)

(58) Field of Classification Search
CPC ................ A61H 3/00; A61H 2201/164; A61H 2201/165; A61H 2201/5053; A61F 2/66;
(Continued)

(56) References Cited

U.S. PATENT DOCUMENTS 9,486,919 B1    11/2016 Thorne et al.
2002/0094919 A1*  7/2002 Rennex .................. A61H 3/008
                                                        482/124
(Continued)

FOREIGN PATENT DOCUMENTS

EP       2 942 162 A2    11/2015
WO    2010/025409 A1     3/2010

OTHER PUBLICATIONS

The International Search Report for PCT/IB2018/055382; dated Oct. 16, 2018; 4 pages.
(Continued)

*Primary Examiner* — Timothy A Stanis
(74) *Attorney, Agent, or Firm* — Vorys, Sater, Seymour and Pease LLP (57) ABSTRACT

Provided is a wearable assisted-walking device including one lower attachment body to the foot defining a lower anchoring point at the heel of the foot of a leg of the user; an upper attachment body to an upper part of the leg proximal from the knee defining an upper ventral anchoring point and an upper dorsal anchoring point arranged on the opposite side of the coronal plane of the user; and an intermediate attachment body defining a first intermediate anchoring point, a second intermediate anchoring point and a third intermediate anchoring point, each anchoring point
(Continued)

Fig. 2 movable respect and connected by cables to the leg; the intermediate attachment body being adapted to store the energy by a relative motion between the anchoring points and then use it for assist walking.

15 Claims, 9 Drawing Sheets

(51) Int. Cl.
*A61F 2/66* (2006.01)
*A61F 2/50* (2006.01)
*A61F 2/60* (2006.01)

(52) U.S. Cl.
CPC . *A61F 2002/503* (2013.01); *A61F 2002/5038* (2013.01); *A61F 2002/607* (2013.01); *A61F 2002/608* (2013.01); *A61F 2002/6642* (2013.01); *A61F 2002/6836* (2013.01); *A61F 2002/6854* (2013.01); *A61H 2201/164* (2013.01); *A61H 2201/165* (2013.01); *A61H 2201/5053* (2013.01)

(58) Field of Classification Search
CPC .................. A61F 2/68; A61F 2002/503; A61F 2002/5038; A61F 2002/607; A61F 2002/6642; A61F 2002/6836; A61F 2002/6854

See application file for complete search history.

(56) References Cited

U.S. PATENT DOCUMENTS

| | | | |
|---|---|---|---|
| 2013/0296746 A1* | 11/2013 | Herr | A63B 21/4015 601/34 |
| 2014/0190289 A1* | 7/2014 | Zhu | B25J 9/104 74/89.22 |
| 2014/0277739 A1 | 9/2014 | Kornbluh et al. | |
| 2016/0128890 A1 | 5/2016 | LaChappelle et al. | |
| 2017/0119613 A1 | 5/2017 | Roh et al. | |
| 2017/0143573 A1* | 5/2017 | Boulanger | A61H 1/0266 |
| 2018/0028390 A1* | 2/2018 | Dietl | A61F 2/60 |
| 2019/0343707 A1* | 11/2019 | Riener | A61H 3/00 |

OTHER PUBLICATIONS

The Italian Search Report for IT 201700084346; completed Mar. 13, 2018; 2 pages.

* cited by examiner

WEARABLE ASSISTED-WALKING DEVICE

The present invention relates to a wearable assisted-walking device of the type specified in the preamble of the first claim.

In particular, the invention relates to a solution for reducing the metabolic cost of human walking, and thus is usable to help a person during locomotion.

It is known that walking is realized by a periodic sequence of muscle activations that generate force positive and negative work/energy/power.

The muscles mainly used for walking are: the iliopsoas (IP), the gluteus maximus (GM), the biceps femoris (BF), the rectus femoris (RF), the vasti (in particular the vastus lateralis VL), the tibialis anterior (AT), the gastrocnemius (in particular the gastrocnemius medialis (MG), the soleus (Sol). Such muscles add to other muscles performing a negligible activity.

During a walking stride these muscles are active, and contribute to the mechanical energy that is absorbed and generated. In conclusion, the muscles of the leg provide positive and negative peak power while walking.

The most relevant and identifiable peak joint powers are: A1: negative power region that corresponds to the eccentric activity of the plantar flexor muscles that surround the ankle from heel-strike through tibial progression; A2: positive power region corresponding to the concentric contraction of the platarflexors during the late stance phase; K1: negative power region, corresponding to the eccentric contraction of the knee extensors during heel-strike; K2: positive power region, corresponding to the concentric knee extensor contraction during mid-stance; K3: negative power region, corresponding to the eccentric contraction in the rectus femoris during late stance; K4: negative power region, corresponding to the eccentric contraction in the biceps femoris during late stance; H1: positive power region, that is not always present, which corresponds to the concentric contraction of the hip flexors during the first half of the stance phase; H2: negative power region, corresponding to the eccentric contraction of the hip flexors during mid-stance; and H3: positive power region, corresponding to the concentric contraction of the hip flexors during pre-swing and initial leg swing.

Given this premise, the currently known wearable assisted-walking devices are identified by the acronym AFO ("Ankle Foot Orthosis").

Such devices usually consist of a shell that is constrained at the ankle or leg, an attachment to the foot and/or the body, joints that allow movement between the shell and attachment, and one or more motorized actuators that simulate the muscles and control the motion between the shell and attachment. The described prior AFOs have some major drawbacks.

Additional drawbacks are the complexity, high costs, and high synchronization required between the device and the user during walking. In order to combat such drawbacks, previous investigators have developed passive wearable assisted-walking devices that do not include a motor. An example of such a wearable assisted-walking device is described in US2013046218 introducing a device taking advantage of the energy produced by the muscles.

In US2013046218 there is a shell attached to the leg and an attachment to the foot that allows a rotational joint, which is comprised of a linear actuator adapted to contract at peak A1. This device also includes spring that is attached to the shell, adapted to store the energy produced by the contraction of the linear actuator in A1, and allowed to control the extension of the linear actuator during pre-swing. Another device is KR20120044683A, which describes a wearable assisted-walking device that takes advantage of a kinematic mechanism similar to that of US2013046218. This device also has some major drawbacks.

One major drawback of this device is that it stores a very small amount of energy and thus is not usable for walking. Therefore, the device makes a limited contribution to assisting walking. The technical task underlying the present invention is to design a wearable assisted-walking device capable of substantially obviating the aforementioned drawbacks.

In the scope of this technical task, it is important that the present invention of a wearable assisted-walking device is passive and capable of taking advantage of the energy produced by the muscles when walking.

It is also important that the wearable assisted walking device does not change the motion of or overload the ankle or other joints.

It is a further objective of the invention to provide a wearable assisted-walking device that is simple, low-cost and easy to use.

In this situation, the technical task underlying the present invention is to devise a wearable assisted-walking device capable of substantially obviating the mentioned drawbacks at least in part.

In the scope of said technical task, it is an important object of the present invention to obtain a wearable assisted-walking device which is motor-free and thus capable of working by maximally taking advantage only of the energy produced by the muscles when walking.

It is another important object of the invention to provide a wearable assisted-walking device which does not excessively overload the ankle or other joint.

It is a further major object of the invention to provide a wearable assisted-walking device which is simple, low-cost and easy to use.

The technical task and the objects specified are achieved by a wearable assisted-walking device as claimed in appended claim 1. Exemplary preferred embodiments are described in the dependent claims.

The characteristics and advantages of the invention are clearly evident from the following detailed description of preferred embodiments of the invention, with reference to the accompanying drawings, in which.

In the present invention, the measurements, values, shapes and geometric references (such as perpendicularity and parallelism), when associated with words such as "about" or other similar words, such as "almost" or "substantially", are to be understood as short of errors of measurement or inaccuracies due to production and/or manufacturing errors, and especially short of a minor divergence from the value, measurement, shape or geometric reference with which it is associated. For example, such words, if associated with a value, preferably indicate a divergence not higher than 10% of the value itself.

Furthermore, when used, words such as "first", "second", "upper", "lower", "main" and "secondary" do not necessarily identify an order, a relationship priority or a relative position but may be simply used to distinguish different components more clearly.

Unless otherwise indicated, the measurements and data shown in the test were performed in International Standard Atmosphere ISA (ISO 2533).

With reference to the Figures, the wearable assisted-walking device according to the invention is indicated by reference numeral 1 as a whole.

It is used to assist walking by acquiring energy during a first motion (in detail prior to and during heel-strike) and returning it during a second motion (in detail during a late stance), preferably not contiguous to the first movement. In particular, the wearable assisted-walking device 1 is adapted to store the energy produced during the extension of the knee and to release the energy in order to provide push-off at the ankle. Specifically, device 1 is adapted to store the energy produced at peak K4 and to release the energy at the subsequent peak A2.

The wearable device 1 is adapted to be worn by a user, such as a person.

The wearable device 1 may comprise at least one lower attachment body 2 to a foot of the user. It preferably comprises two lower bodies 2 that are each adapted to be attached to each foot of the user.

Each lower body 2 defines a lower anchoring point 2a at the heel of each foot.

In this document, the term "anchoring point" identifies a constraining point of a cable (described below) which prevents it from sliding (with respect to the anchoring point, and thus to the body to which it is constrained). The anchoring point may allow a rotation of the cable or alternatively define an integral constraint for the cable.

The lower body 2 may be a known as the lower attachment body to the foot. An example of such a lower body 2 is the "lower portion 108" described and shown in US 20130046218.

The wearable device 1 may comprise at least one upper body 3, preferably only one, suitable to be attached in an integral manner to an upper part of the leg of the user, i.e. proximal from the knee.

The "upper part of the leg" defines in this document the part of leg above the knee. The upper body 3 may be constrained to the torso, in particular to the abdomen, and specifically at the waist of the user. In this case, device 1 may comprise an additional upper body 4 (identifiable in one band) adapted to be attached to the user's thigh and defining one or more sliding slots for one or more cables described below for each lower body 2.

The upper body 3 defines an upper ventral anchoring point 3a (namely a frontal anchoring point), and an upper dorsal anchoring point 3b (namely a rear anchoring point) for each lower body 2.

In detail the upper attachment body 3 is suitable to be attached to the dorsal part of the back, above the gluteal muscles, defining for each of the attachment below the knee (see the intermediate body 5 below described), an upper ventral anchoring point 3a arranged on the opposite site of the coronal plane of the user.

In use, i.e. when device 1 is worn by the wearer, the upper ventral anchoring point 3a and the upper dorsal anchoring point 3b are on opposite sides of the user's coronal plane.

The upper body 3 may comprise a belt.

The wearable device 1 may comprise an intermediate attachment body 5 to the user's leg.

Preferably the intermediate attachment body 5 is suitable to be attached to the user below the knee, i.e. to the shank or the lower limb portion between knee and foot.

The wearable device 1 may comprise an intermediate attachment body 5 for each lower body 2.

Preferably, the intermediate body 5 is adapted to be constrained at the gastrocnemius muscle.

Figure 1A:
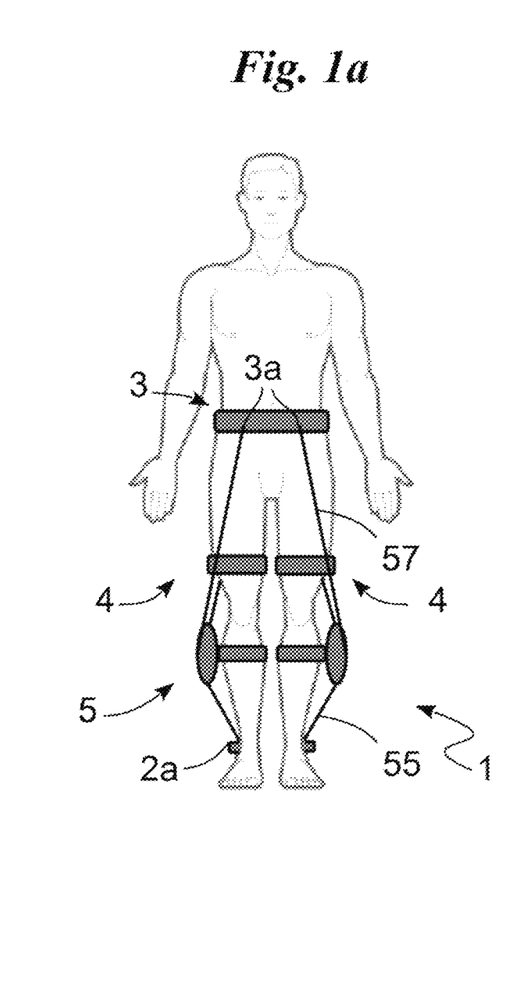
FIG. 1a-1c show a wearable assisted-walking device according to the invention.
Figure 1B:
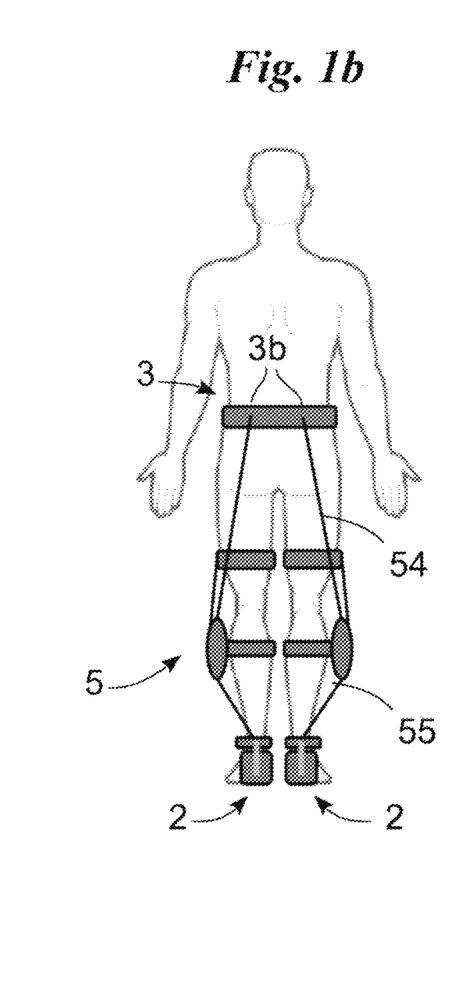
Figure 1C:
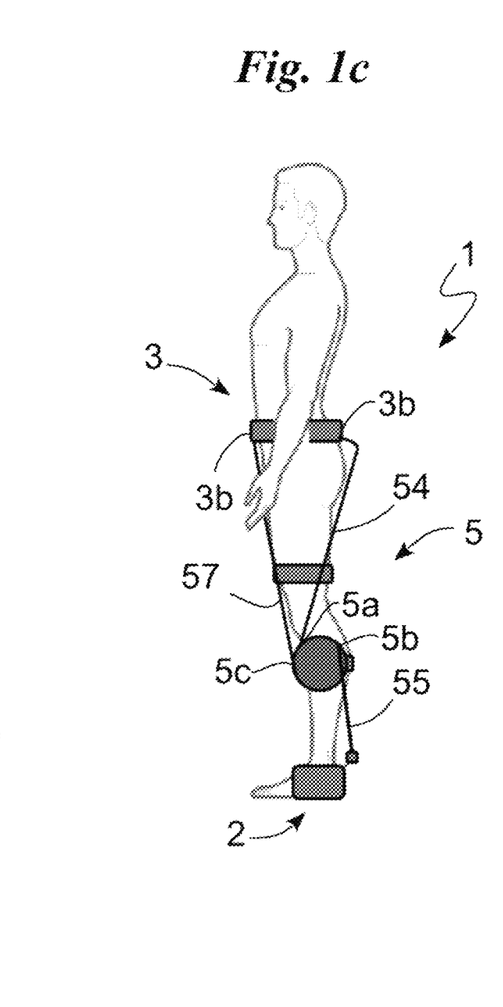
Figure 2:
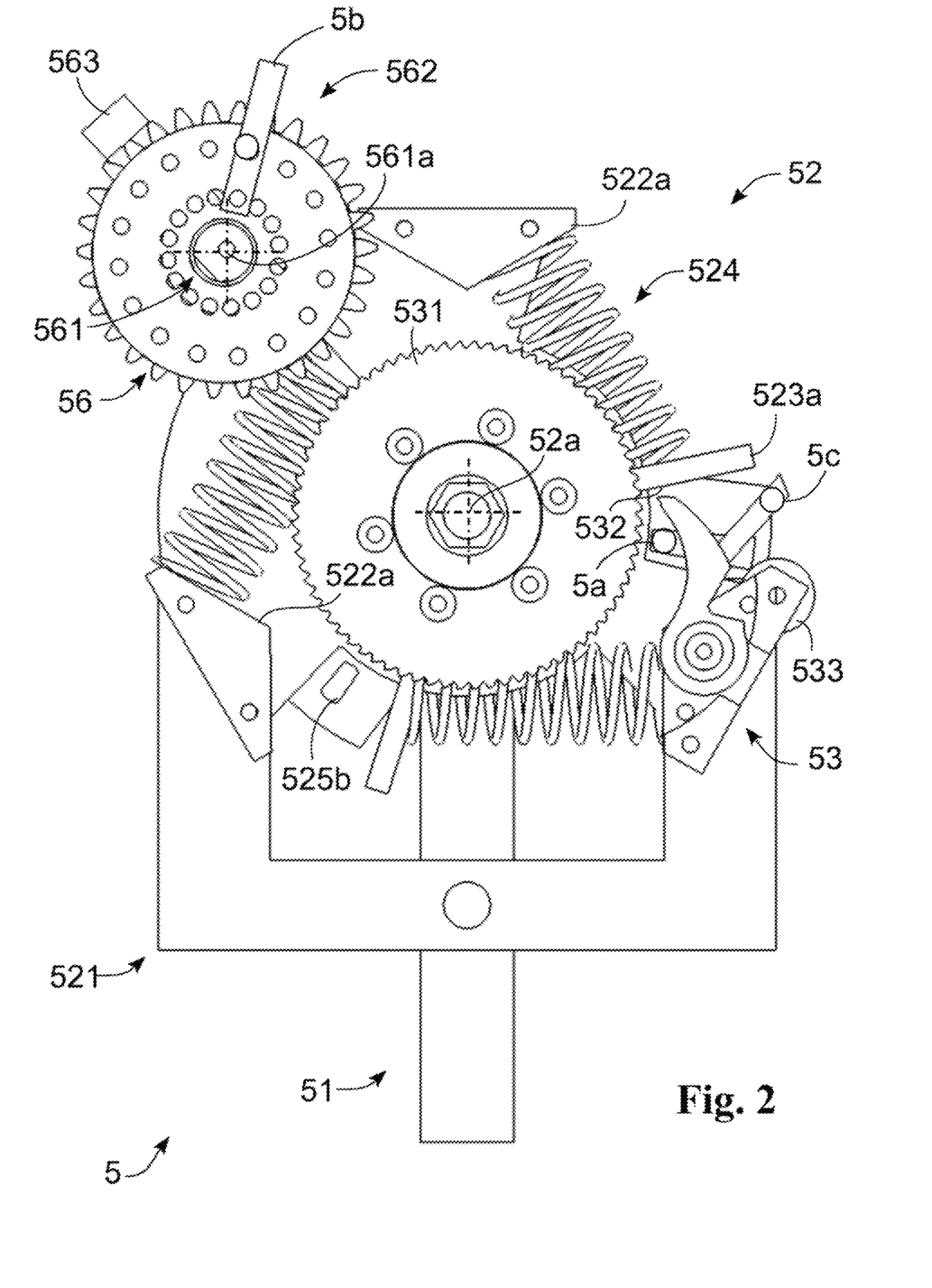
FIG. 2 presents a part of the wearable assisted-walking device.
Figure 3:
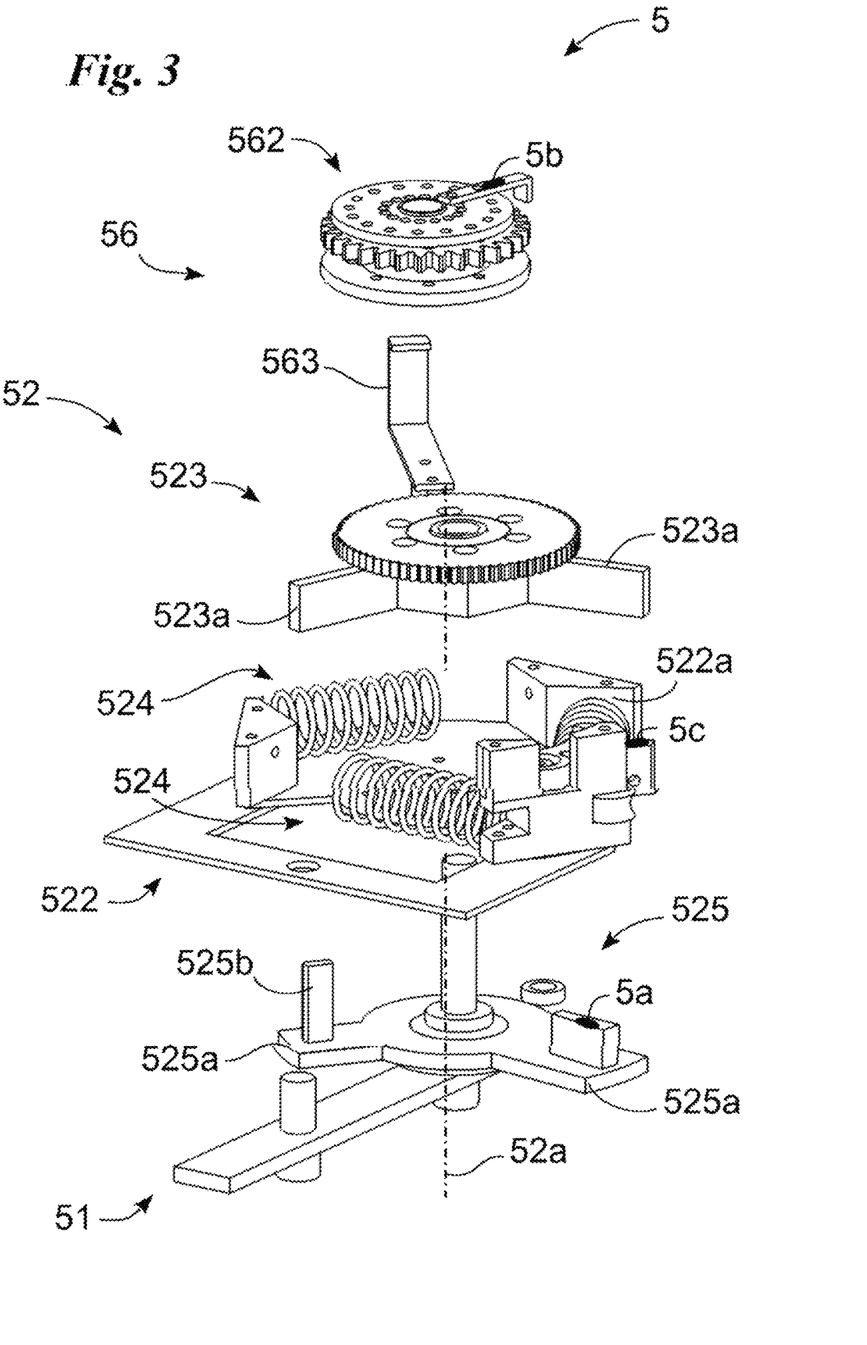
FIG. 3 illustrates an exploded view of FIG. 2.

The intermediate body 5 (FIG. 2-3) may comprise an attachment 51 adapted to be attached, preferably integrally, to the leg, e.g. by a band.

The attachment 51 is adapted to be attached, preferably integrally, to the lower part of the leg and preferably to the shank. We highlight "lower part of the leg" defines in this document the part of leg below the knee.

The intermediate body 5 may comprise a kinematic storage mechanism 52 adapted to store energy and defining a first intermediate anchoring point 5a which is movable with respect to the attachment 51 and a second intermediate anchoring point 5b also movable with respect to the attachment 51.

In use, the first intermediate anchoring point 5a and the second intermediate anchoring point 5b are at the leg, and more precisely near the gastrocnemius muscle.

In detail in use, the intermediate anchoring points 5a and 5b are attached on opposite sides with respect to the user's coronal plane. Preferably, the first intermediate anchoring point 5a is dorsal (namely frontal), while the second intermediate anchoring point 5b is ventral (namely rear with respect to said coronal plane).

The kinematic storage mechanism 52 connects the first intermediate anchoring point 5a and the second intermediate anchoring point 5b in order to store the energy by taking advantage of a motion of the first intermediate anchoring point 5a with respect to the attachment 51 and to release that energy by causing the movement of the second intermediate anchoring point 5b with respect to the attachment 51.

The kinematic storage mechanism 52 stores energy by means of a movement thereof according to a loading direction and releases energy by means of a movement thereof according to a releasing direction opposite to the loading direction.

The kinematic storage mechanism 52 may define a rotation axis 52a so as to have, for example, the loading and releasing directions which are counterclockwise and clockwise, respectively.

In use, the rotation axis 52a is substantially parallel to the coronal plane, and more precisely substantially perpendicular to the user's sagittal plane.

The kinematic storage mechanism 52 comprises a pin 521 that defines the rotation axis 52a; a stator 522 that does not rotate about the rotation axis 52a; a rotor 523 that is adapted to rotate about the rotation axis 52a with respect to the stator 523; and at least one storage unit 524 interposed between stator 522 and rotor 523 that takes advantage of the reciprocal rotation in order to store and/or release energy.

In particular, the kinematic storage mechanism 52 may comprise multiple storage units 524, preferably three, angularly and equally spaced apart with respect to the rotation axis 52a.

The storage unit 524 is adapted to store energy by deforming elastically. It is a spring adapted to store energy, preferably by varying its length. More specifically, the storage unit 524 is a compression spring.

The stator 522 is integral with the attachment 51.

For each storage unit 524, stator 522 defines a resting surface 522a for the storage unit 524 against which said unit 524 is compressed when storing energy.

Rotor 523 is adapted to rotate idly about the rotation axis 52a, e.g. by virtue of bearings/bronze bearings interposed between rotor 523 and pin 521.

For each storage unit 524, rotor 523 comprises an arm 523a adapted to enclose the storage unit 524 between the arm 523a itself and a resting surface 522a that causes either storage or release of energy by means of its rotation.

Rotor 523 preferably comprises multiple arms 523a, three in detail, equally and angularly spaced apart.

The intermediate anchoring points 5a and 5b are associated with the rotor 523, so that rotor 523 controls the storage of energy when it is pulled by the first point 5a, and rotor 523 controls the displacement of the second intermediate anchoring point 5b when it is pulled by the storage unit 524.

The first intermediate anchoring point 5a and the second intermediate anchoring point 5b are constrained (either directly or indirectly) to rotor 523 conveniently at discrete arms 523a.

In particular, the first intermediate anchoring point 5a is integral with an arm 523a. Alternatively, the kinematic storage mechanism 52 comprises a feeding block 525 with which the first intermediate anchoring point 5a is integral and adapted to rotate about the rotation axis 52a thus feeding the rotor 523 at least when it is moved in the loading direction.

The feeding block 525 comprises one or more additional arms 525a, one of which being integral with the first intermediate anchoring point 5a; and a connector 525b integral with an additional arm 525a and adapted to contact an arm 523 thus allowing the feeding block 525 to feed rotor 523 when it is moved in the loading direction.

It is worth noting that the rotor 523, when moved in the releasing direction, feeds the feeding block 525.

Preferably, the feeding block 525 and the rotor 523 are spaced apart along the rotation axis 52a and enclose said stator 522.

The second intermediate anchoring point 5b is integral with an arm 523a, discrete from that with which the first intermediate anchoring point 5a is associated.

In order to ensure the release of energy only at the desired time, the intermediate body 5 may comprise a locking system 53 of the kinematic storage mechanism 52 adapted to selectively prevent or permit the energy release.

The locking system 53 defines a third intermediate anchoring point 5c at attachment 51, movable with respect to attachment 51.

In use, the third intermediate anchoring point 5c is on the same side as the first point 5a with respect to the coronal plane.

The third intermediate anchoring point 5c is on the side opposite to the second intermediate anchoring point 5b with respect to the first intermediate anchoring point 5a.

As a function of the position of the third intermediate anchoring point 5c with respect to attachment 51, the locking system 53 defines a locking portion, where the motion of the kinematic storage mechanism 52 is prevented in the releasing direction, and a releasing position, where the motion of the kinematic storage mechanism 52 is allowed in the releasing direction and thus allows the release of the energy.

The locking system 53 does not interfere with the kinematic storage mechanism 52 which allows the motion in the loading direction in both locking position and releasing position.

In brief, in locking position, the locking system 53 prevents the motion of rotor 523 in the releasing direction and preferably allows the motion of rotor 523 in the loading direction; while in the releasing position, it allows the motion of rotor 523 in the loading and releasing directions.

The locking system 53 can be identified as a known ratchet and pawl that can be controlled by the third anchoring point 5c. It comprises a toothed wheel 531 adapted to rotate about the rotation axis 52a and integral with rotor 523; at least one tooth 532 adapted to engage the toothed wheel 532 defining the locking portion and/or to be disengaged from the toothed wheel 532 defining the releasing position.

In some cases, the locking system 53 may comprise thrust means, such as a preloading spring, adapted to override the engagement of tooth 532 with the toothed wheel 531.

Tooth 532 is hinged to stator 522 in order to rotate about an axis preferably substantially parallel to the rotation axis 52a.

The third intermediate anchoring point 5c is constrained and, in detail, integral with the tooth 532, in order to control the switch to the releasing position.

The intermediate body 5 may comprise a loading cable 54 connecting the upper dorsal anchoring point 3b to the first intermediate anchoring point 5a thus allowing the kinematic storage mechanism 52 to store the energy on the basis of a first motion between the upper body 3 and the intermediate body 5.

Figures 4A, 5A:
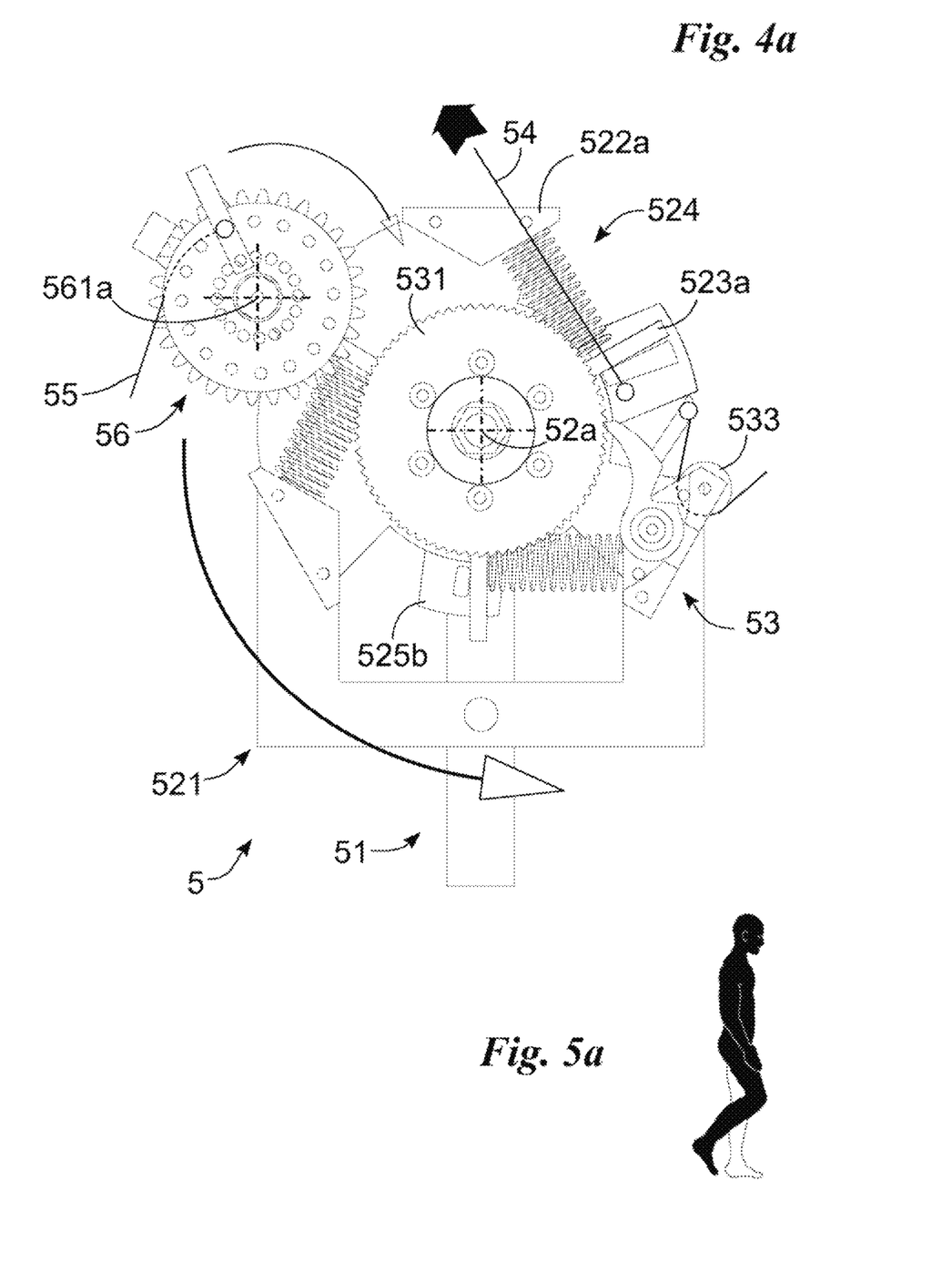
FIG. 4a-4f illustrate a sequence of operations of the assisted-walking device according to the invention.
FIG. 5a-5f the captions show the phase of a walking stride that the device corresponds to in the sequence shown in FIGS. 4a-4f.
Figures 4B, 5B:
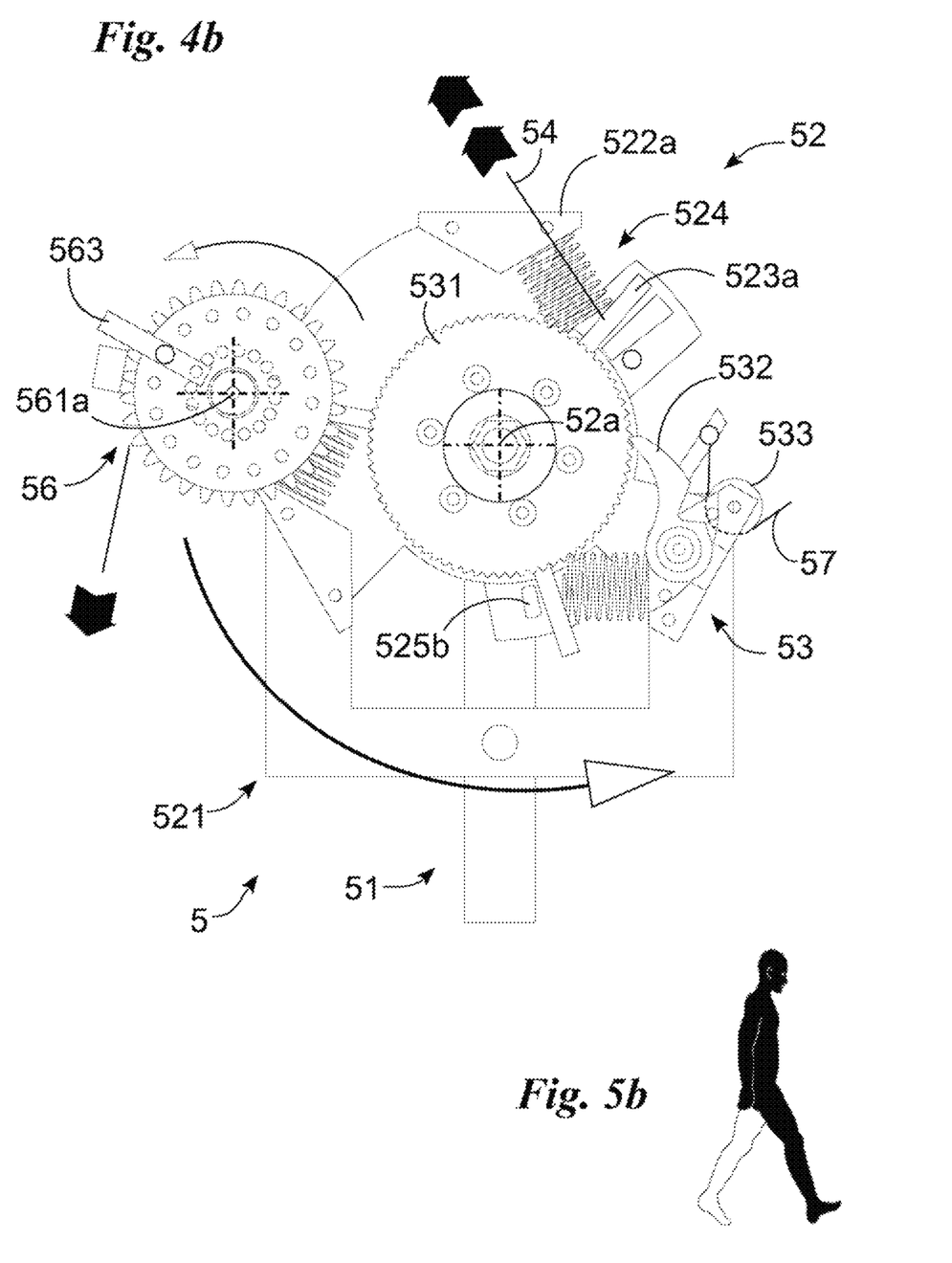

The first motion (FIG. 5a-5b) is provided by the movement of the first intermediate anchoring point 5a with respect to the intermediate body 5 and controlled by the displacement of the upper dorsal attachment point 3b with respect to the intermediate body 5. In use, such a motion occurs with the extension of the knee and more precisely at peak K4.

The loading cable 54 may be rigid and thus not flexible. Alternatively, it may be flexible.

The intermediate body 5 may comprise a discharging cable 55 connecting the lower anchoring point 2a to the second intermediate anchoring point 5b thus allowing the kinematic storage mechanism 52 to release the energy and cause motion of the lower body.

The discharging cable 55 may be rigid and thus not flexible. Alternatively, it may be flexible. In order to ensure the correct tensioning, the discharging cable 55 is flexible (especially in the case of flexible cable 5), the intermediate body 5 may comprise a tensioner 56 adapted to adjust the tension of the discharging cable 55 irrespective of the position of the second intermediate anchoring point 5b with respect to the attachment 51, and thus keeping the flexible discharging cable 55 taut, for example.

The discharging cable 55 may be rigid and thus not flexible. Alternatively, it may be flexible.

In order to ensure the correct tensioning, the discharging cable 55 is flexible (especially in the case of flexible cable 5), the intermediate body 5 may comprise a tensioner 56 adapted to adjust the tension of the discharging cable 55 irrespective of the position of the second intermediate anchoring point 5b with respect to the attachment 51, and thus keeping the flexible discharging cable 55 taut, for example.

Tensioner 56 is constrained to rotor 523 and, in detail, to an arm 523a.

It may comprise a hinge 561 defining an additional rotational axis 561a; an attachment 562 adapted to rotate about the additional rotation axis 561a to which the second intermediate anchoring point 5b and said discharging cable 55 are constrained; and a preloaded spring engaged with the attachment 562 and controlling a rotation of the attachment 562 about the additional rotation axis 561a thus keeping the discharging cable 55 taut.

The additional rotation axis 561*a* is substantially parallel to the rotation axis 52*a*.

Hinge 561 is integral with rotor 523, and in detail with an arm 523*a*.

The preloaded spring is a spiral spring having one end integral with the hinge 531 and the other end integral with the attachment 562.

In some cases, tensioner 56 may comprise a travel stop 563 against which the attachment 562 abuts during the energy release.

The travel stop 563 is integral with rotor 523, and in detail with an arm 523*a*. It also defines a radial extension of the constraining arm 523*a* of the tensioner 56 adapted to limit the travel of the attachment 562, and thus of the second intermediate anchoring point 5*b*, in the releasing direction. In use, the travel stop 563 allows the release of energy to the lower body 2 only after the heel lifts from the ground.

The intermediate body 5 may comprise a releasing cable 57 connecting the upper ventral anchoring point 3*a* to the third intermediate anchoring point 5*c* in order to control the switching of the locking system 53 from the locking position to the releasing position due to a second motion between upper body 3 and intermediate body 5.

The releasing cable 57 may be rigid and thus not flexible. Alternatively, it may be flexible.

The second motion is successive and not contingent on the first motion.

Figures 4C, 5C:
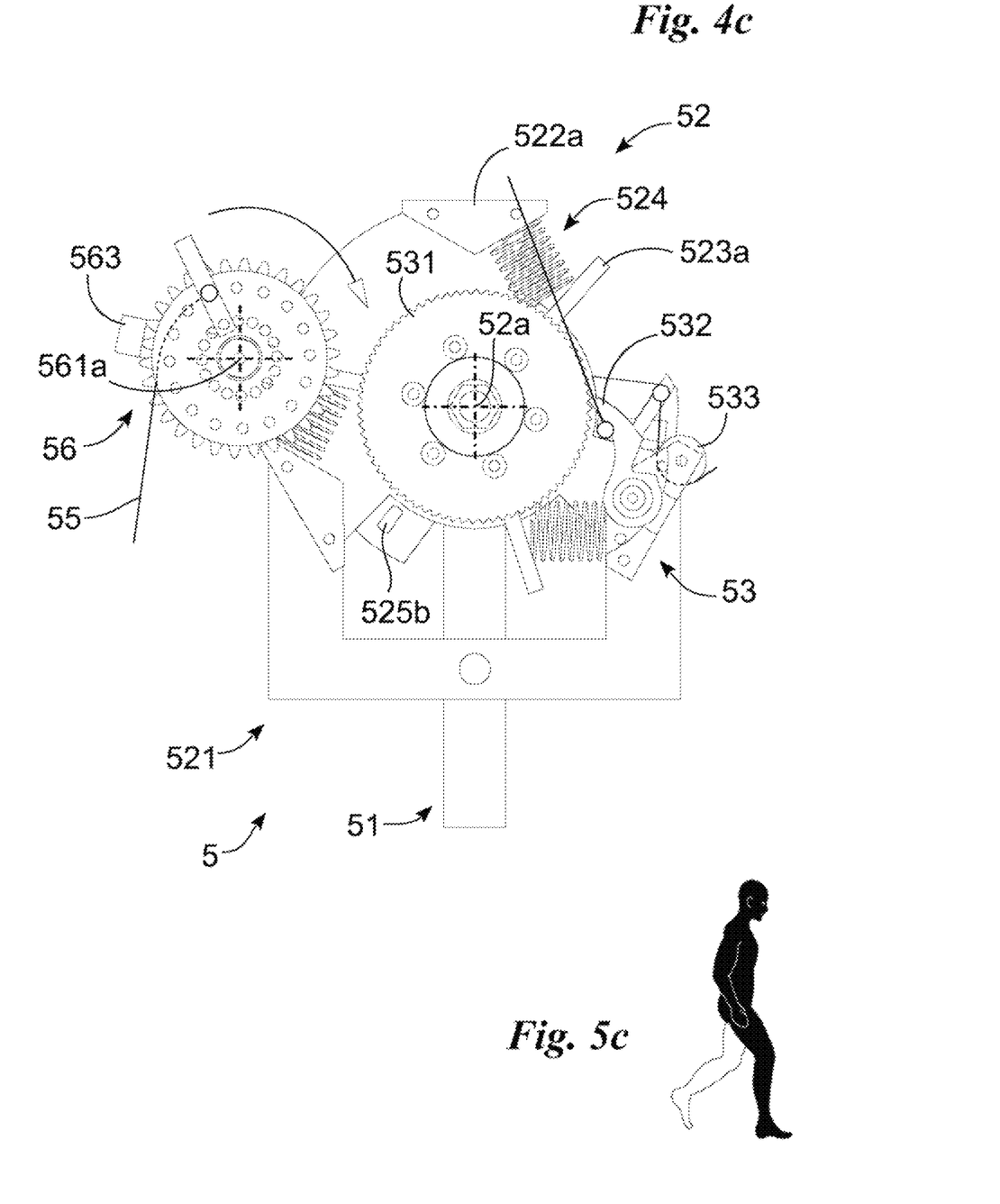
Figures 4D, 5D:
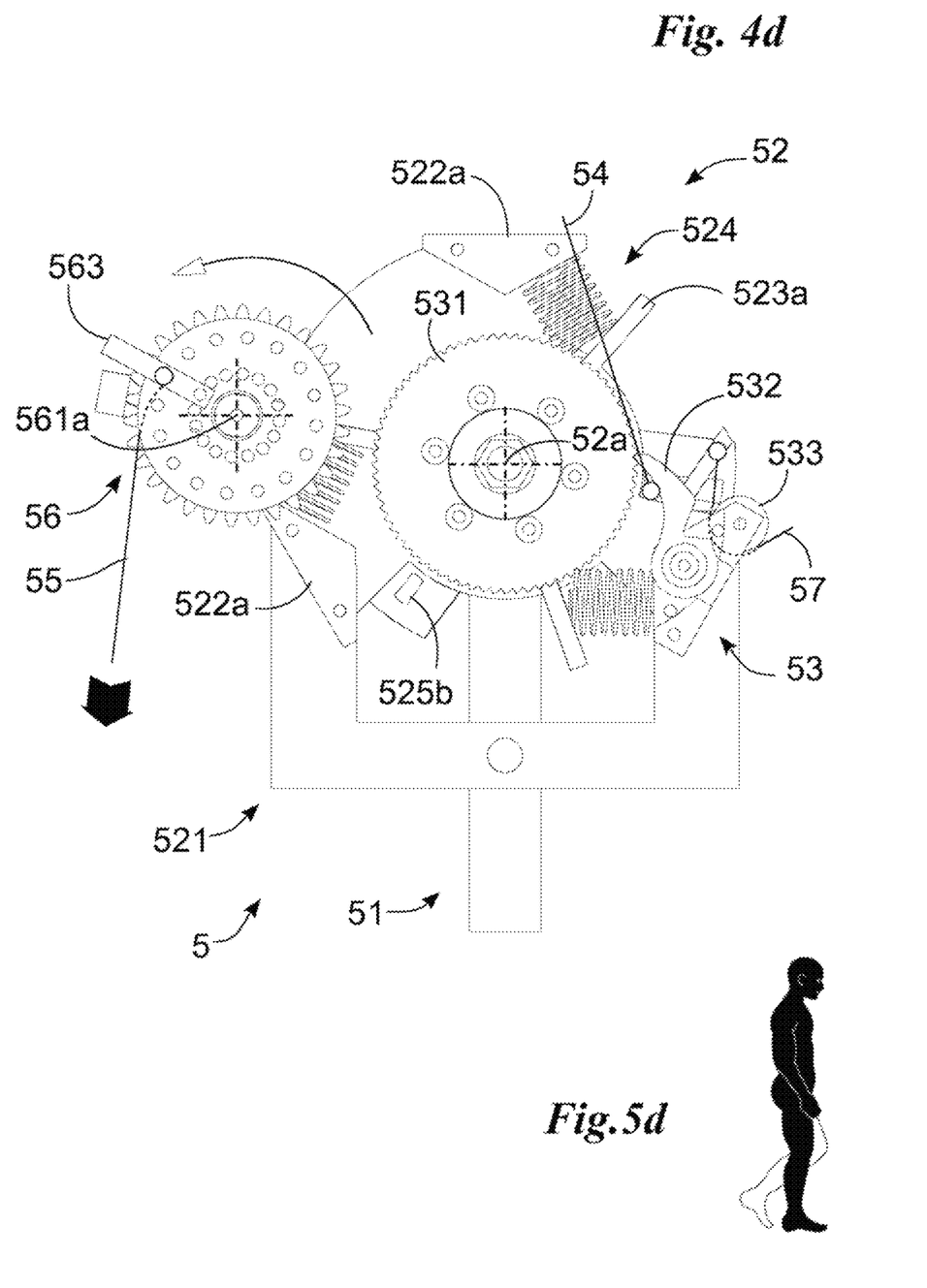
Figure 5E:
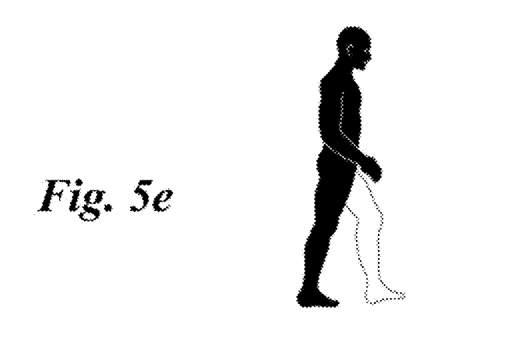
Figure 5F:
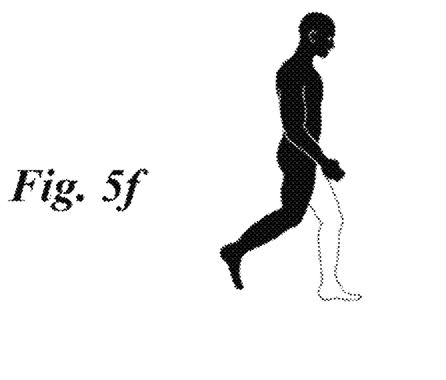

The second motion (FIG. 5*d*-5*e*) is given by the movement of the third intermediate anchoring point 5*c* with respect to the intermediate body 5 controlled by a displacement of the upper dorsal attachment point 3*a* with respect to the intermediate body 5. This second motion substantially starts with the bending of the knee and occurs at peak A2.

In order to release energy during this second motion, the locking system 53 may comprise a transmission pulley 533 of the releasing cable 56 conveniently hinged to the intermediate body 5 and, in detail, to the stator 522.

Pulley 533 is on the opposite side with respect to the upper dorsal anchoring point 3*a* with respect to the third intermediate anchoring point 5*c*.

The invention identifies a new assisted-walking method that can be implemented by the wearable assisted-walking device 1 described above in structural terms.

Figure 4E:
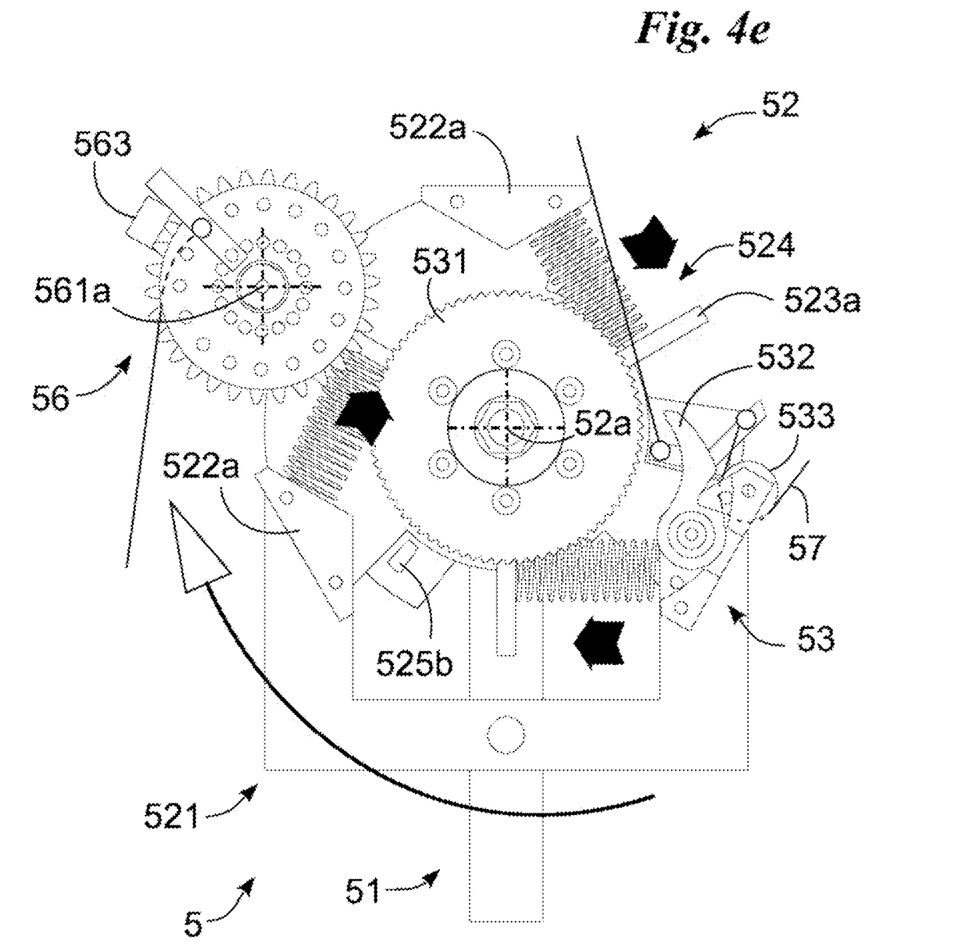
Figure 4F:
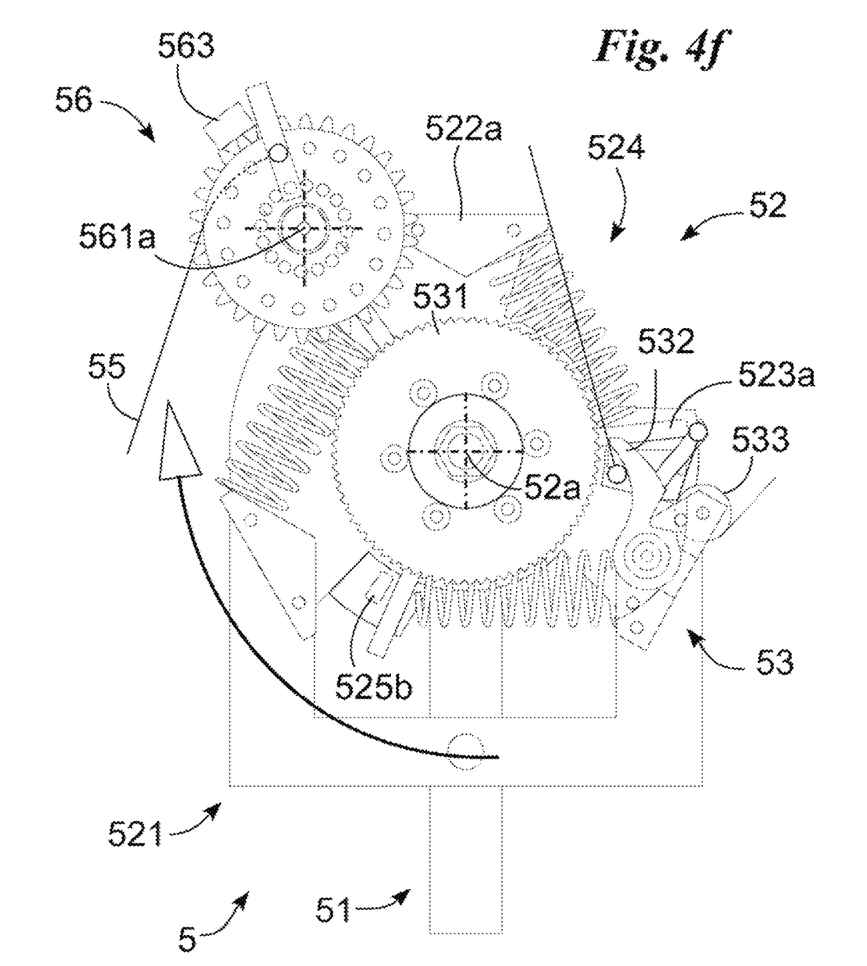

The assisted-walking method comprises a step of loading (FIG. 4*a*-4*b*), in which the energy is stored in the kinematic storage mechanism 52; and a step of releasing (FIG. 4*d*-4*f*), in which the energy is released to the lower body 2 by the kinematic storage mechanism 52.

During the step of loading, there is a first motion between intermediate body 5 and upper body 3, which tends to move the first intermediate anchoring point 5*a* and the upper dorsal attachment point 3*b* away from each other. In response to the first motion, the loading cable 54 is pulled and controls the rotation in the loading direction of rotor 523 with respect to stator 522 about the rotation axis 52*a*.

More precisely, the loading cable 54 rotates the additional arms 525*a* which, by virtue of connector 525*b*, rotate the arms 523*a*, and thus the rotor 523.

The rotation of the arms 523*a* pushes the storage unit 524 against the resting surface 522*a* and the springs are compressed when storing energy.

During the rotation of the arms 523*a* in the loading direction, tensioner 56 keeps the discharging cable 55 taut.

During the step of loading, the locking system 53 may be in locking position.

Having concluded the step of loading, the step of releasing (FIG. 4*d*-4*e*) may start, in which the second motion takes the locking system 53 from the locking position to the releasing position and thus the kinematic storage mechanism 52 (FIG. 4*f*) discharges the energy stored in the step of loading.

During the step of releasing, there is the second motion between intermediate body 5 and upper body 3 which tends to move the third intermediate anchoring point 5*a* and the upper dorsal attachment point 3*b* mutually away from each other. Therefore, the releasing cable 57 is pulled, and conveniently by virtue of the transmission defined by the pulley 533, controls the release of the tooth 532 from the toothed wheel 532 and thus puts the locking system 53 in releasing position.

At this point, the rotation of rotor 523 in the releasing direction is no longer prevented by the locking system 53 and thus the storage unit 524 releases the stored energy by controlling the rotation of the arms 523*a* in the releasing direction.

The loading cable 55, being the second intermediate anchoring point 5*b* fed by an arm 523*a*, pulls the lower anchoring point 2*a* towards the intermediate body 5 and thus promotes powered plantar-flexion of the ankle.

It is worth noting that between the step of loading and the step of releasing, the assisted-walking method advantageously comprises a step of storage (FIG. 4*c*) in which the locking system 53, while remaining in the locking position, prevents the energy stored in the preceding step of loading from being discharged.

The wearable assisted-walking device 1 according to the invention achieves major advantages.

A first advantage is that the wearable device 1 identifies a solution for storing energy at a joint (the knee) and releases this energy at a different joint (the ankle) while not getting in the way of the user.

Such an aspect is allowed by the particular choice of the constraint points of the bodies 2, 3 and 5, and thus of the various anchoring points 2*a*, 3*a*, 3*b*, 5*a*, 5*b* and 5*c* and by how they are connected by cables 54, 55 and 57.

Furthermore, this innovative technical solution allows one to take advantage of particular walking movements (more precisely, the peaks K4 and A2) for the storage and return of energy.

Another advantage of the wearable device 1 is the utilization of large contributions of energy that are always present during walking. While passive devices cannot supply power capable of sufficiently helping the user, active devices require large motors and big batteries to provide this power, but are heavy, large and uncomfortable.

A further advantage 1 is that the wearable device 1, by being passive (free from motors and batteries), is light and does not require electronic control.

The invention is susceptible to variants falling within the scope of the inventive concept defined by the claims. In such a scope, all the details can be replaced by equivalent elements and materials of any shape and size.

The invention claimed is:

1. A wearable assisted-walking device adapted to be worn by a user, comprising:
   at least one lower attachment body for a foot of a leg of the user defining a lower anchoring point at a heel of the foot of the leg of the user;
   an upper attachment body for an upper part of the leg proximal from a knee defining, for each said lower attachment body, an upper ventral anchoring point and an upper dorsal anchoring point arranged on an opposite side of the coronal plane of the user; and for each said lower attachment body, an intermediate attachment body, comprising:
- an attachment adapted to be integrally constrained to the leg of the user;
- a kinematic storage mechanism defining, at the leg, a first intermediate anchoring point movable with respect to the attachment and a second intermediate anchoring point movable with respect to the attachment; the kinematic storage mechanism being adapted to store the energy taking advantage of a motion of the intermediate anchoring point with respect to the attachment and to release energy causing a movement of the intermediate anchoring point with respect to the attachment;
- a locking system defining, at the leg, a third intermediate anchoring point movable with respect to the attachment; the locking system defining, as a function of the position of the third intermediate anchoring point, a locking position, in which the locking system prevents the kinematic storage mechanism from releasing the energy, and a releasing position, in which the locking system allows the kinematic storage mechanism to release the energy;
- a loading cable connecting the upper dorsal anchoring point to the first intermediate anchoring point allowing the kinematic storage mechanism to store the energy on the basis of a first motion between the upper body and the intermediate body;
- a discharging cable connecting the lower anchoring point to the second intermediate anchoring point allowing the kinematic storage mechanism to release the energy causing a motion of the lower body; and
- a releasing cable connecting the upper ventral anchoring point to the third intermediate anchoring point so as to control the switching of the locking system from the locking position to the releasing position on the basis of a second motion between the upper body and the intermediate body.

2. The wearable device according to claim 1, wherein the third intermediate anchoring point is on a side opposite to the second intermediate anchoring point with respect to the first intermediate anchoring point.

3. The wearable device according to claim 2, wherein the locking system comprises a toothed wheel integral with a rotor; at least one tooth adapted to engage the toothed wheel defining the locking position or to be disengaged from the toothed wheel defining the releasing position.

4. The wearable device according to claim 3, wherein the locking system comprises a transmission pulley of the releasing cable hinged to the intermediate body on a side opposite to the upper ventral anchoring point with respect to the third intermediate anchoring point.

5. The wearable device according to claim 2, wherein the locking system comprises a toothed wheel integral with a rotor; at least one tooth adapted to engage the toothed wheel defining the locking position or to be disengaged from the toothed wheel defining the releasing position.

6. The wearable device according to claim 5, wherein the locking system comprises a transmission pulley of the releasing cable hinged to the intermediate body on the side opposite to the upper ventral anchoring point with respect to the third intermediate anchoring point.

7. The wearable device according to claim 1, wherein the kinematic storage mechanism comprises a pin defining a rotation axis; a stator integral with the attachment; a rotor adapted to rotate about the rotation axis with respect to the stator; and at least one storage unit interposed between the rotor and the stator in order as to take advantage of a reciprocal rotation between the rotor and the stator to store and release energy; wherein the first intermediate anchoring point is associated with the rotor in order to control the rotation of the rotor and thus the storage of energy by the storage unit; and wherein the second intermediate anchoring point is associated with the rotor so that the storage unit releases energy by rotating the rotor and the second intermediate anchoring point.

8. The wearable device according to claim 7, wherein the second intermediate anchoring point is integrated with the rotor; wherein the kinematic storage mechanism comprises a feeding block of the rotor; and wherein the intermediate anchoring point is integrated with the feeding block.

9. The wearable device according to claim 8, wherein the feeding block and the rotor are spaced apart along the rotation axis and enclose the stator therebetween.

10. The wearable device according to claim 1, wherein the intermediate attachment body comprises a tensioner adapted to adjust the tension of the discharging cable irrespective from a position of the second intermediate anchoring point with respect to the attachment.

11. The wearable device according to claim 10, wherein the tensioner comprises a hinge defining an additional rotation axis; an attachment adapted to rotate about the additional rotation axis and to which the second intermediate anchoring point and the discharging cable are constrained; and a preloaded spring controlling a rotation of the attachment adapted to tension the discharging cable.

12. The wearable device according to claim 11, wherein the tensioner comprises a travel stop adapted to limit the travel of a counter-attachment and integrated with the rotor.

13. The wearable device according to claim 1, wherein the kinematic storage mechanism comprises a pin defining a rotation axis; a stator integral with the attachment; a rotor adapted to rotate about the rotation axis with respect to the stator; and at least one storage unit interposed between the rotor and the stator in order as to take advantage of a reciprocal rotation between the rotor and the stator to store and release energy; wherein the first intermediate anchoring point is associated with the rotor in order to control the rotation of the rotor and thus the storage of energy by the storage unit; and wherein the second intermediate anchoring point is associated with the rotor so that the storage unit releases energy by rotating the rotor and the second intermediate anchoring point.

14. The wearable device according to claim 13, wherein the second intermediate anchoring point is integrated with the rotor; wherein the kinematic storage mechanism comprises a feeding block of the rotor; and wherein the intermediate anchoring point is integrated with the feeding block.

15. The wearable device according to claim 14, wherein the feeding block and the rotor are spaced apart along the rotation axis and enclose the stator therebetween.

* * * * *